US010772610B2

(12) United States Patent
Dai (10) Patent No.: US 10,772,610 B2
(45) Date of Patent: Sep. 15, 2020

(54) SAMPLE COLLECTION DETECTOR

(71) Applicant: Hangzhou D2 Technology CO., LTD., Hangzhou (CN)

(72) Inventor: Jielin Dai, Hangzhou (CN)

(73) Assignee: Hangzhou D2 Technology CO., LTD., Hangzhou (CN)

( * ) Notice: Subject to any disclaimer, the term of this patent is extended or adjusted under 35 U.S.C. 154(b) by 195 days.

(21) Appl. No.: 15/899,852

(22) Filed: Feb. 20, 2018

(65) Prior Publication Data

US 2018/0235582 A1     Aug. 23, 2018

(30) Foreign Application Priority Data

Feb. 22, 2017    (CN) ..................... 2017 2 0158417 U
Nov. 10, 2017    (CN) ........................ 2017 1 1106194
Nov. 10, 2017    (CN) ..................... 2017 2 1499652 U
Nov. 10, 2017    (CN) ..................... 2017 2 1502963 U (51) Int. Cl.
     *A61B 10/00*      (2006.01)

(52) U.S. Cl.
     CPC ................................ *A61B 10/0038* (2013.01)

(58) Field of Classification Search
     CPC .............. A61B 10/0038; A61B 10/007; A61B 10/0045; A61B 5/1405; A61B 5/15003; A61B 5/150389; A61B 5/1427; A61B 5/1438; A61B 5/150351; A61B 5/153; A61B 2010/0216; A61B 10/0291; A61B 2017/320012; A61B 10/02; G01N 1/12; G01N 2001/1037; G01N 1/2035; G01N 1/08; G01N 2001/1006; G01N 1/2273;
G01N 1/405; G01N 2001/2223; G01N 2001/028; G01N 35/1002; G01N 21/03; G01N 21/82; B01L 3/5029; B01L 3/508; B01L 3/04; B01L 3/5082; B01L 3/50825; B01L 2300/042; B01L 2400/0406
USPC ............ 73/863.21, 864.64, 864.63; 600/573, 600/575, 577, 578, 569; 422/411, 557, 422/550, 547; 436/165
See application file for complete search history.

(56) References Cited

U.S. PATENT DOCUMENTS

| | | | | |
|---|---|---|---|---|
| 5,514,341 A | * | 5/1996 | Urata ................. | A61B 10/0038 422/534 |
| 2006/0216830 A1 | * | 9/2006 | Kikuiri ............. | A61B 10/0038 436/165 |
| 2008/0286831 A1 | * | 11/2008 | Liang ................. | A61B 10/0096 435/34 |

(Continued)

*Primary Examiner* — John Fitzgerald
*Assistant Examiner* — Truong D Phan
(74) *Attorney, Agent, or Firm* — Jiangqiong Liu (57) ABSTRACT

The present invention provides a sample collection detector, comprising a sampling device, a detecting device and a communicating device, wherein the sampling device has a sampling chamber and a sample feeding rod, the sample feeding rod is inserted into the sampling chamber to finish sampling; the communicating device has a sample feeding channel that is in communication with the sampling chamber and detecting device, a valve assembly is provided between the sample feeding channel and the sampling chamber, the valve assembly is initially closed, the sample feeding channel is separated from the sampling chamber, the sample feeding rod triggers the valve assembly to open and communicate the sample feeding channel and the sampling chamber.

14 Claims, 9 Drawing Sheets

(56) References Cited

U.S. PATENT DOCUMENTS

| | | | | |
|---|---|---|---|---|
| 2009/0004058 A1* | 1/2009 | Liang | ............... | A61B 10/0096 |
| | | | | 422/68.1 |
| 2009/0215159 A1* | 8/2009 | Kirby | ................ | B01L 3/502 |
| | | | | 435/287.2 |
| 2015/0292986 A1* | 10/2015 | Frost | ............... | A61B 10/0038 |
| | | | | 422/549 |

* cited by examiner

SAMPLE COLLECTION DETECTOR

RELATED APPLICATIONS

This application claims priority to Chinese Application Serial No. CN201720158417.X, filed Feb. 22, 2017, Chinese Application Serial No. CN2017111061943, filed Nov. 10, 2017, Chinese Application Serial No. CN20172015029552, filed Nov. 10, 2017, Chinese Application Serial No. CN2017215029637, filed Nov. 10, 2017, Chinese Application Serial No. CN201721499652X, filed Nov. 10, 2017; Chinese Application Serial No. CN2017217312122, filed Dec. 12, 2017; and Chinese Application Serial No. CN2017217329602 filed Dec. 12, 2017. Each of the referenced applications are herein incorporated by reference in their entirety.

FIELD OF THE INVENTION

The present invention relates to a device for detecting analytes in a fluid sample, in particular, to a sample collection detector for sampling and testing of stools.

BACKGROUND OF THE INVENTION

The following background art is provided to assist readers in understanding the present invention and should not be construed as prior art.

Sample analysis and detection is a prerequisite to a number of tests and treatments in the medical and biological fields.

The stool testing is one of the routine laboratory tests. For the stool testing, usually the examinees should retain the stools and hospital professionals are responsible for testing. However, since the storage and delivery of stool samples propose high requirements and examinees in the hospital often ignore or have no intention of stools, the stool sampling and testing rate is low during the actual screening and physical examination.

The main reasons for low testing rate of stools are as follows: first, the stool is easy to contaminate, and we are not willing to look directly or contact with the stool; second, the stool is solid, which needs to be fully dissolved in a buffer solution before immunodetection test; third, the sampling size of stool is difficult to control; fourth, it is required to ensure no spillage of stool solution during testing operations.

At present, no appropriate device for stool testing is available. Some manufacturers manufacturing the immunosensitive fecal occult blood reagents design their own toilet apparatus, but it has no sampling control device. Fecal solution is opened for tests. Professionals will dissolve feces in a container with a buffer solution, and place the fecal solution to another container, insert test strips into the container for testing. The fecal solution is opened during testing, and the detector is scattered, inconvenient to carry and transport; and non-professionals cannot perform tests by themselves.

Therefore, it is necessary to improve the conventional apparatus for detecting stool samples, to overcome the above shortcomings, so that users can use them more conveniently.

SUMMARY OF THE INVENTION

The object of the present invention is to provide a sample collection detector capable of integrating the sample collection and detection and achieving closed detection of sample mixture.

A sample collection detector, comprising a sampling device, a detecting device and a communicating device, wherein the sampling device has a sampling chamber and a sample feeding rod, the sample feeding rod is inserted into the sampling chamber to finish sampling; the communicating device has a sample feeding channel that is in communication with the sampling chamber and detecting device, a valve assembly is provided between the sample feeding channel and the sampling chamber, the valve assembly is initially closed, the sample feeding channel is separated from the sampling chamber, the sample feeding rod triggers the valve assembly to open and communicate the sample feeding channel and the sampling chamber.

The valve assembly is a unit that separates or communicates the sampling channel with the sample feeding channel.

As a preferred solution, the valve assembly comprises a valve chamber, a push rod and a sealing part, the valve chamber is connected with the sampling chamber and the sample feeding channel, and the sealing part seals the outlet of the valve chamber; the communicating device has provided a space for inserting the push rod. The space is a chamber for the push rod.

Preferably, the push rod comprises a receiving portion and a sample-passing portion, and the receiving portion matches with the bottom of the sample feeding rod. When the sample feeding rod triggers the valve assembly to open, the sample-passing portion makes the sealing part to open the outlet of the valve chamber.

Preferably, after quantitative delivery of samples, the sealing portion seals the outlet of the valve chamber, the sealing portion is located between the receiving portion and the sample-passing portion, and the sealing portion is in interference fit with the outlet of the valve chamber. The outer surface of the sample-passing portion is provided with an axial sample-passing groove; or, there is a gap between the sample-passing portion and the valve chamber. The gap between the sample-passing groove or sample-passing portion and the valve chamber forms a flow path, through which the sample mixture flows into the communicating device. By setting the length of the sample-passing portion, the size of the sample-passing groove, or the size of the gap between the sample-passing portion and the valve chamber, the quantitative delivery of the liquid samples is achieved.

Preferably, the receiving portion is a piston, the piston has a disc-shaped fin extending outward, and the disc-shaped fin is a flexible part. When pressing the valve chamber, the disc-shaped fin produces deformation to seal the inlet of the valve chamber, thus the piston and sealing portion achieve dual-sealing of the valve chamber.

Preferably, the receiving portion has a socket adapted to the sample feeding rod.

Preferably, the sealing part comprises a plug that independently plugs the valve chamber. During use, the sample rod triggers the push rod, and the sample-passing portion of the push rod will push the plug away from the valve chamber, and liquid samples will enter the detecting device from the sample-passing portion.

Alternatively, the sealing part comprises a plug mounted on the push rod. During use, the sample feeding rod triggers the push rod, when the plug leaves the outlet of the valve chamber, the sample-passing portion reaches the valve chamber outlet. The liquid sample enters the detecting device from the sample-passing portion, and the push rod continues to operate, the sealing portion seals the valve chamber outlet, to complete the sample delivery.

Alternatively, the sealing part further comprises a barrier film disposed at the outlet of the valve chamber, to enhance the reliability of the sealing part. The plug is inside and the barrier film is outside, to achieve dual sealing and separation of the sampling chamber and the detecting device. The "inside, outside" herein is relative to the valve chamber. When the push rod is operating, the plug will pierce the barrier film completely, to avoid the inaccurate quantification of samples caused by complete or partial sealing of sample feeding channel by the barrier film.

The sampling device can achieve quantitative sampling.

As a preferred solution, the sampling chamber is provided with a baffle, and the area between the baffle and the valve assembly forms a sample mixing sub-chamber, and the baffle is provided with a sample-passing hole to allow the insertion of a sample feeding rod; the sample feeding rod comprises a loading portion and an inserting portion, and the loading portion and the sample-passing hole form a quantitative sampling unit. The inserting portion has an increased diameter in a direction away from the loading portion, and the inserting portion seals the sample-passing hole. By setting the distance of the gap between the loading portion and sample-passing hole, the samples that can enter the sample mixing sub-chamber are quantified.

Preferably, a guide sleeve is disposed below the baffle, the guide sleeve is located at the sample-passing hole, and the guide sleeve is integrated with the baffle.

The detecting device can accommodate the sample mixture and testing element, so that the sample mixture is adsorbed by the testing element.

As a preferred solution, the detecting device has a detection chamber, the detection chamber is adjacent to the sampling chamber, and the detection chamber is provided with a testing element mounting rack. The "adjacent" includes "horizontally adjacent" and "vertically adjacent".

Preferably, the testing element mounting rack is integrated with the valve chamber and a stripping position is on the testing element mounting rack.

Preferably, the testing element mounting rack separates the detection chamber into detection sub-chambers for accommodating the testing element, and the detection sub-chamber communicates with the sample feeding channel.

Preferably, the testing element mounting rack is provided with a mounting slot, and the mounting slot communicates with a communicating mechanism. The testing element is placed in the mounting slot and the testing element is inserted into the sample sub-chamber. The sample mixture is absorbed by the testing element, to complete the testing.

Preferably, the detection chamber has an accessory sub-chamber, the accessory sub-chamber is adjacent to the detection sub-chamber, and the accessory sub-chamber communicates with the detection sub-chamber via a hole.

In order to prevent triggering delivery of samples by the valve assembly due to mistaken operation, an anti-misoperation component is provided between the sample delivery device and the detecting device.

As a preferred solution, the sampling chamber is located on the side of the detection chamber, the sample feeding rod is detachably connected to a limiting cover, and when the limiting cover is combined with the sample feeding rod, the limiting cover is abutted against the detection chamber. Therefore, when the limiting cover is used as an anti-misoperation component and the limiting cover is combined with the sample feeding cover, the sample feeding rod is unable to trigger the valve assembly; only when the limiting cover is removed from the sample feeding rod, the sample feeding rod can operate and trigger the valve assembly, to achieve anti-misoperation.

As a preferred solution, the sample feeding rod has a convex block thereon, the sampling chamber has a limiting portion for abutting the convex block and an operating portion for guiding the convex block. When the convex block matches with the limiting portion, the sample feeding rod is away from the valve assembly and unable to trigger the valve assembly; only when the convex block matches with the operating portion, the convex block runs along the operating portion, and the sample feeding rod triggers the opening of the valve assembly. By this way, the convex block, limiting portion and operating portion can achieve anti-misoperation.

Preferably, the limiting portion is provided with a groove for accommodating the convex block and abutting a stop portion of the convex block; the groove is located on the sampling chamber.

Preferably, the operating portion is a notch on the wall of the sampling chamber, and the notch allows the convex block to operate therein.

Preferably, the sampling chamber is located on the side of the detection chamber, and the operating portion is located between the sampling chamber and the detection chamber.

As a preferred solution, a thread pair is arranged between the sample feeding rod and the sampling chamber, and the thread pair is located on the baffle. In the initial state, the sample feeding rod is limited by the thread pair at the position away from the valve assembly. Only when the sample feeding cover is rotated by an external force can the sample feeding rod move down along the thread pair to open the valve assembly.

Preferably, the detection chamber is located on the side of the sampling chamber, the sample feeding rod has a thread segment and a polish segment, the polish segment is on the thread segment, and the polish segment is detachably provided with an anti-misoperation block, on one end of which is a flexible buckle and another end is a rigid block. When the anti-misoperation block is combined with a sample feeding rod, the detection chamber abuts against the rigid block. The flexible buckle is clamped with the polish segment, while the rigid block is abutted by the detecting device to limit the displacement.

In order to further ensure that the valve assembly is not triggered by the misoperation, the flexible buckle of the anti-misoperation block is stuck in the polish segment of the anti-misoperation portion, and the rigid block is restricted to move downward by the detecting device. When the flexible buckle is combined with the polish segment, the sample feeding cover cannot drive the sample feeding rod to move downward. Only when the flexible buckle is removed from the polish segment will the sample feeding rod be able to move down while rotating.

Beneficial Effects

The present invention can achieve the following beneficial effects:

First, a sample-passing portion and a sealing portion are provided on the push rod, to achieve the quantitative delivery of samples.

Second, the quantitative sampling unit can achieve the precise definition of the sample size.

Third, the valve chamber is sealed by a plug, and the plug can be completely separated from the valve chamber, so that the valve chamber is fully open, to avoid the interference of the sample flow by the barrier film and guarantee the quantitative delivery of samples.

Fourth, the valve chamber is integrated with the testing element mounting rack, and the testing element has a large length and size, facilitating stripping.

Fifth, the detection chamber is located on the side of the sampling chamber, and the communicating device communicates with the detection chamber 2-1 and the sampling chamber from the bottom, to achieve integrated quantitative sampling and testing of samples.

DETAILED DESCRIPTION OF THE EMBODIMENTS

The structures involved in this invention or the used technical terms are further described below. These descriptions are only to explain how to achieve the ways in this invention through examples, and will not restrict this invention.

Detection

Detection means to assay or test the presence or absence of a substance or material, including but not limited to chemical substances, organic compounds, inorganic compounds, metabolic products, medicines or drug metabolites, organic tissues or metabolites of organic tissues, nucleic acids, proteins or polymers. Additionally, detection means to test the quantity of a substance or material. Furthermore, assay also means immunodetection, chemical detection, enzyme detection, and etc.

Testing Element

Various testing elements can be combined and applied to this invention. The testing element comprises a test strip, which can be analyzed in various forms such as immunoassay or chemical test to detect such analyte in samples as drugs or relevant metabolites indicating physical conditions. In some forms, the test strip is a water absorbent material having sample adding area, reagent area and testing result area. Samples are added to the adding area, and flow to the reagent area under the capillary action. In the reagent area, samples dissolve the reagent and mix with it to detect analyte (if there is analyte in samples). And samples with reagents continue to flow to the testing result area. Other reagents are fixed in the testing result area, and these reagents react and combine with analyte (if there is analyte in samples) or the first type of reagent in the reagent area. In the noncompetitive detection form, if there is analyte in samples, signals will be generated; and if not, signals will not be generated. In the competitive detection form, if there is no analyte in samples, signals will be generated; and if not, signals will not be generated. The invention applies to various analytic forms.

When the testing element is a test strip, it can be made from water absorbent or non-water absorbent materials. A test strip can use various materials to transmit liquid, and one material can be superposed on another material. For example, a filter paper can be superposed on the nitrocellulose. Or in the test strip, a region that at least contains one material is located behind the other region that at least contains a different material. In such case, the liquid circulates among regions, and they can be superposed on one another or choose not to superpose. Materials on the test strip can be fixed on, for example, the holder of a plastic liner or hard surface, to enhance the holding force of the test strip.

In some embodiments where some detected objects are detected through a signal generation system (for example, at least one enzyme reacts specifically with the detected object), at least one substance generating signals can be absorbed on the analyte detecting area of the test strip, just like being absorbed specifically on the materials of the test strip as described above. In addition, substances generating signals in the sample adding area, reagent area and analyte detecting area of the test strip or all over the whole test strip can be pretreated in advance on one or more materials of the test strip, which can be achieved by adding the solution of substances generating signals to the surface of the application area or soaking one or more materials of the test strip in the signal solution, after which dry the test strip. Moreover, the above method can be used to pretreat substances generating signals in the sample adding area, reagent area and analyte detecting area of the test strip or all over the whole test strip in advance on one or more materials of the test strip. Furthermore, the signal substance existing in the sample adding area, reagent area and detecting area of the test strip can be added to one or more surfaces of the test strip materials as the labeling reagent.

Areas of the test strip can be arranged as follows: a sample adding area, at least a reagent area, at least a testing result area, at least a control area, or at least an adulteration detecting area and a liquid absorption area. If the detecting area comprises a control area, the preferred control area is located behind the analyte detecting area of the testing result area. All these areas or their combinations can be on a single test strip containing a material. Additionally, these areas are made from different materials, and are connected together according to the transmission direction of liquid. For example, liquid can be transmitted directly or indirectly among different areas. In this embodiment, different areas can be connected end to end or superposed mutually along the direction of liquid transmission, or connected through other materials such as connecting medium materials (water absorbent materials such as filter paper, glass fiber or nitrocellulose are preferred). By use of the connecting materials, the liquid can flow on materials that connect each area end to end, materials that connect each area end to end but the liquid does not flow, or materials that each area is overlapped mutually (including but not limited to overlapping from end to end) but the liquid does not flow.

If the test strip contains an adulteration detecting control area, the area can be arranged before or after the result detecting area. When the result detecting area contains a control area, the adulteration control area is preferred to be arranged before the control area. In one embodiment of this invention, the test strip is used for analytical judgment and/or control of adulteration. The adulteration control area can be arranged before or after the control area, and preferably, before the control area.

In particular embodiments of the invention, the testing element or test strip may be located at a carrier of the testing element. The carrier may be a testing element mounting rack as shown in the figure. Preferably, it is located at the carrier of the testing element, for example, a mounting slot of a testing element mounting rack.

Samples

The detection apparatus provided in the invention can be used to detect samples including biological liquid (such as case liquid or clinical samples). The liquid sample or fluid sample can come from solid or semi-solid samples, including excreta, biological tissues and food samples, and these solid or semi-solid samples can be converted to liquid samples by using any suitable methods such as mixing, crushing, macerating, incubating, dissolving or digesting the solid samples in a suitable solution (such as water, phosphate solution or other buffer solutions) with the enzymolysis. "Biological samples" comprise samples from animals, plants and food, such as urine, saliva, blood and its components, spinal fluids, vaginal secretion, sperms, excrement, sweat, secreta, tissues, organs, tumors, cultures of tissues and organs, cell cultures and media from human or animals. The preferred biological sample is stools; food samples comprise food processed substances, final products, meat, cheese, liquor, milk and drinking water; and plant samples comprise samples from any plants, plant tissues, plant cell cutures and media. "Environmental samples" come from the environment (such as liquid samples coming from lake or other water bodies, sewage samples, soil samples, underground water, sea water and effluent samples), and can also comprise waste water or other sewage water. Any analyte can be detected by using this invention and a suitable testing element. Preferably, this invention is used to detect the analytes in the stools.

Analyte

The analytes detected in the present invention include but not limited to creatinine, bilirubin, nitrite, (non-specific) proteins, hormones (such as human chorionic gonadotropin, progesterone hormone, follicle-stimulating hormone), blood, leucocytes, sugar, heavy metals or toxins, bacterial substances (such as proteins or sugar substances against specific bacteria, such as *Escherichia coli* 0157:H7, *Staphylococcus, Salmonella, Fusobacterium, Campylobacter, L. monocytogenes, Vibrio* or *Bacillus cereus*) and substances relevant with the physiological features in the stools samples, such as pH and specific gravity.

Sample Collection Detector

Figure 1A:
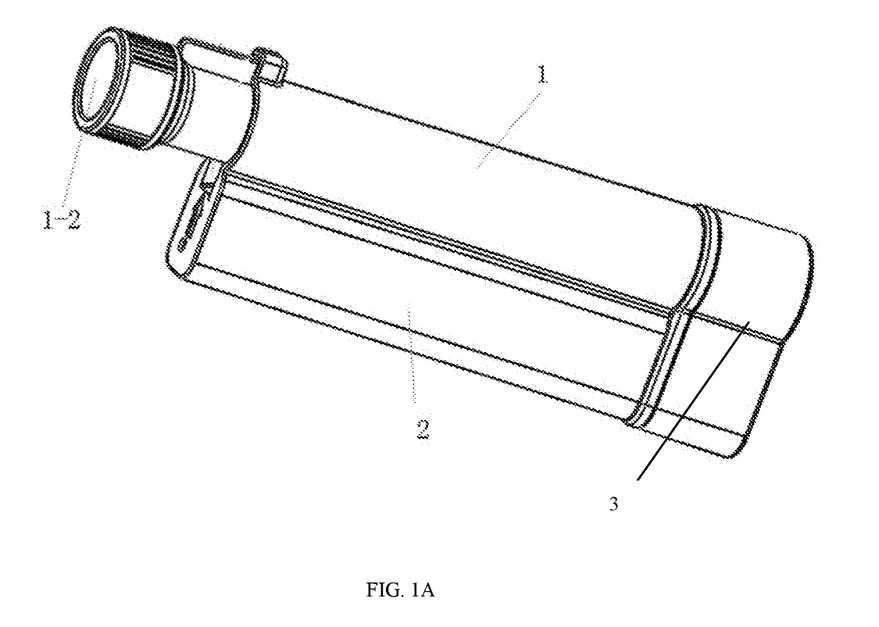
FIG. 1A is a perspective view according to one embodiment of the present invention.
Figure 2A:
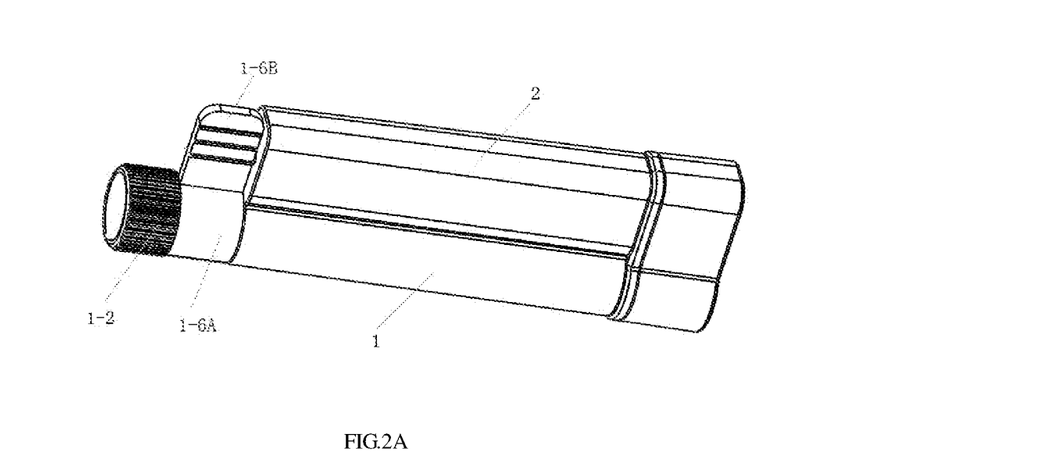
FIG. 2A is a perspective view according to a second embodiment of the present invention.

The sample collection detector, comprising a sampling device 1, detecting device 2 and communicating device 3, is shown in FIG. 1A and FIG. 2A. The sampling device has a sampling chamber 1-1 and a sample feeding rod 1-2, the sample feeding rod 1-2 is inserted into the sampling chamber 1-1 to finish sampling; the communicating device has a sample feeding channel 4003 that is in communication with the sampling chamber 1-1 and the detecting device, a valve assembly is provided between the sample feeding channel and the sampling chamber 1-1, as shown in FIG. 1A. The valve assembly is initially closed, the sample feeding channel is separated from the sampling chamber 1-1, the sample feeding rod 1-2 triggers the valve assembly to open and communicate the sample feeding channel and the sampling chamber 1-1.

When sampling, hold the head of the sample feeding rod 1-2 and insert the tail of the sample feeding rod 1-2 into the solid or semi-solid samples to collect samples. Inject buffer solution in the sampling chamber 1-1, and insert the sample feeding rod 1-2 and the samples into the sampling chamber 1-1, and mix the sample with the buffer solution to form a sample mixture. When the valve assembly is opened, the sample mixture is sent from the sampling chamber 1-1 to the detecting device, and the testing element absorbs the sample mixture for testing of analytes.

Valve Assembly

In the present invention, the valve assembly separates the sampling channel 4003 from the sample feeding channel to prevent delivery of samples to the detecting device when closed; and when opened, the valve assembly communicates the sampling channel and the sample feeding channel, to feed samples to the detecting device. Initially, the valve assembly is in a closed state.

In some embodiments, as shown in FIG. 1B, FIG. 2B, FIG. 3A, FIG. 3B and FIG. 4, the valve assembly comprises a valve chamber 4-1, a push rod 4-2 and a sealing part 4-3, the valve chamber 4-1 is connected with the sampling chamber 1-1 and the sample feeding channel, and the sealing part 4-3 seals the outlet 5003 of the valve chamber 4-1. The push rod 4-2 has a receiving portion 4-21 that receives the triggering of the sampling rod and a rod body that opens the sealing part 4-3. The receiving portion 4-21 is in contact with the bottom end of the sample feeding rod 1-2. When the valve assembly is opened, the receiving portion 4-21 is pushed by the sample feeding rod 1-2, and rod body makes the sealing part 4-3 to open, then the valve chamber 4-1 is opened, the sample mixture flows through the valve chamber 4-1 into the sample feeding channel, to send samples to the detecting device.

Figure 4:
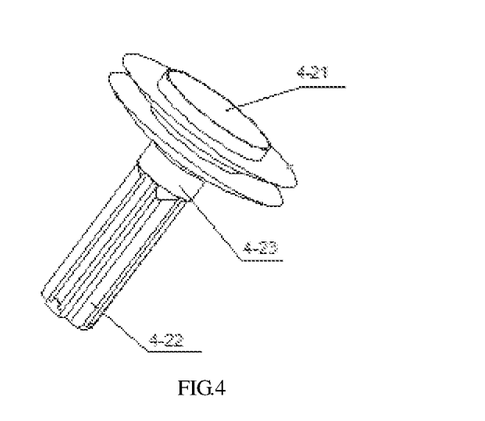
FIG. 4 is a perspective view of a push rod according to one embodiment of the present invention.
Figure 5:
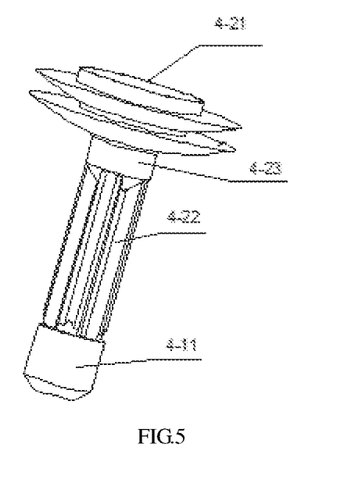
FIG. 5 is a perspective view of a push rod and a plug according to one embodiment of the present invention.

In some preferred embodiments, as shown in FIG. 4, the rod body of the push rod 4-2 has a sample-passing portion 4-22, and there is a space between the sample-passing portion 4-22 and the valve chamber 4-1 that allows the sample mixture to pass through. When the sample feeding rod 1-2 triggers the valve assembly to open and the sealing part 4-3 opens the valve chamber 4-1, the sample mixture reaches the sample feeding channel along the sample-passing portion 4-22.

In some preferred embodiments, as shown in FIG. 4, the rod body of the push rod has a sealing portion 4-23, the sealing portion 4-23 is located between the receiving portion 4-21 and the sample-passing portion 4-22, and the sealing portion 4-23 has a size of interference fit with the outlet 5003 of the valve chamber 4-1. After quantitative delivery of samples, the sealing portion 4-23 closes the outlet of the valve chamber 4-1, and the sampling chamber 1-1 is separated from the sample feeding channel again. The sealing portion 4-23 has a size of interference fit with the outlet of the valve chamber so that the sealing portion can block the outlet of the valve chamber.

In some preferred embodiments, as shown in FIG. 4, a sample-passing groove is provided on the outer surface of the sample-passing portion 4-22. The sample-passing groove forms a flow path, through which the sample mixture flows into the communicating device. By setting the length of the sample-passing portion 4-22, the size of the sample-passing groove, or the size of the gap between the sample-passing portion 4-22 and the valve chamber 4-1, the quantitative delivery of the liquid samples is achieved. Quantitative sample delivery can ensure that the amount of sample mixture conveyed to the detecting device 2 can meet the sample volume required for testing element, and no sample mixture will leak out of the detection chamber caused by excessive sample mixture retained in the detection chamber.

In some preferred embodiments, as shown in FIG. 4, the receiving portion 4-21 is a piston, the piston has a disc-shaped fin extending outward, and the disc-shaped fin is a flexible part. When pressing the valve chamber 4-1, the disc-shaped fin produces deformation to seal the inlet of the valve chamber 4-1, thus the piston and the sealing portion 4-23 achieve dual-sealing of the valve chamber 4-1. The receiving portion 4-21 has a socket adapted to sample feeding rod 1-2.

Figure 6:
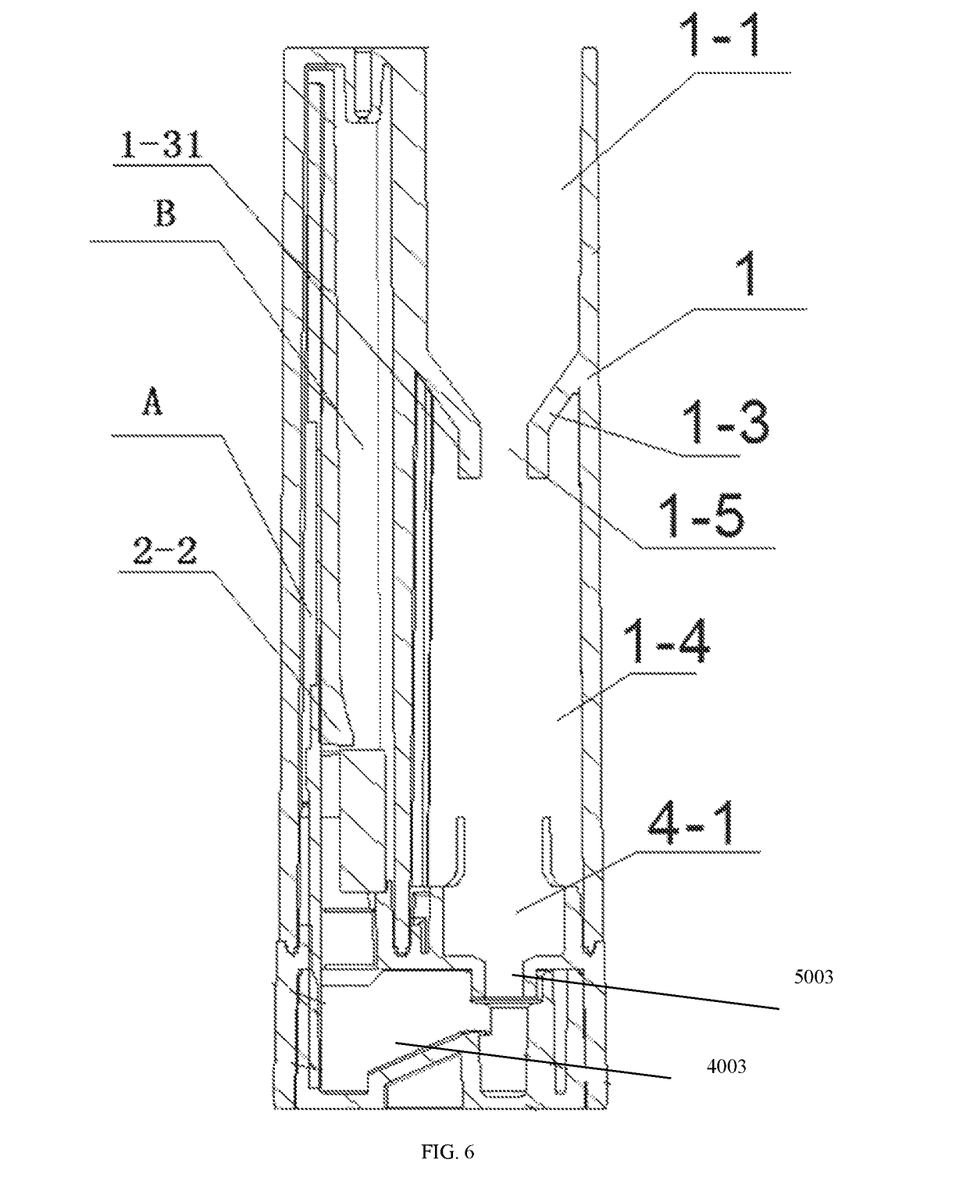
FIG. 6 is a cross-sectional view of a sampling chamber, a detection chamber and a communicating mechanism according to one embodiment of the present invention.

In some preferred embodiments, as shown in FIG. 6, a piston rack 4-4 is provided on the valve chamber, a guide groove is provided on the piston rack 4-4, and the receiving portion 4-21 runs along the guide groove. When the sample feeding rod 1-2 pushes the receiving portion 4-21 to run, the guide groove guides the receiving portion 4-21.

Figure 3A:
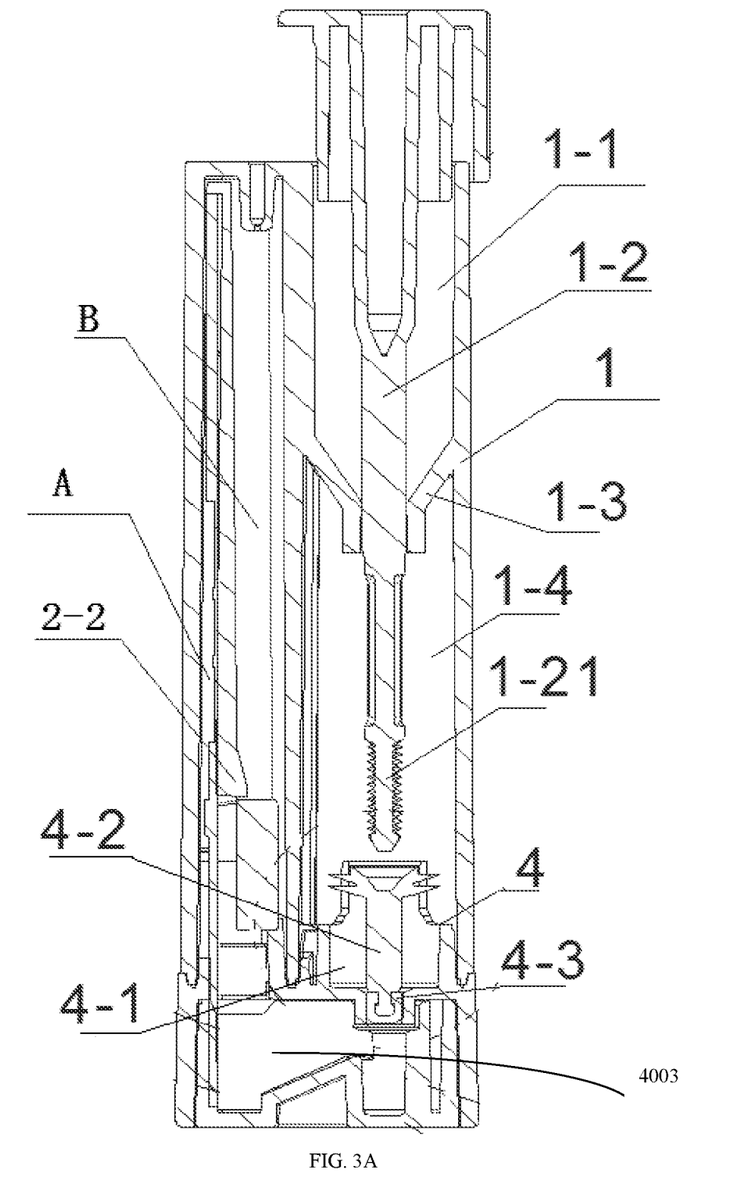
FIG. 3A is a cross-sectional view according to a third embodiment of the present invention.

In some preferred embodiments, as shown in FIG. 3A, the sealing part 4-3 is a plug that independently plugs the valve chamber 4-1. When in use, the push rod 4-2 is triggered by the sample feeding rod 1-2. The sample-passing portion 4-22 of push rod 4-2 pushes the plug away from valve chamber 4-1, then the liquid samples enter the detecting device from the sample-passing portion 4-22.

Alternatively, as shown in FIG. 4, the sealing part 4-3 is a plug mounted on push rod 4-2. The sample-passing portion 4-22 is located between the sealing portion 4-23 and the plug. During use, the sample feeding rod 1-2 triggers the push rod 4-2, when the plug leaves the outlet of the valve chamber 4-1, the sample-passing portion 4-22 reaches the outlet of the valve chamber 4-1. The liquid sample enters the detecting device from the sample-passing portion 4-22, and the push rod 4-2 continues to operate, the sealing portion 4-23 seals the outlet of the valve chamber 4-1, to complete the sample delivery.

Figure 3B:
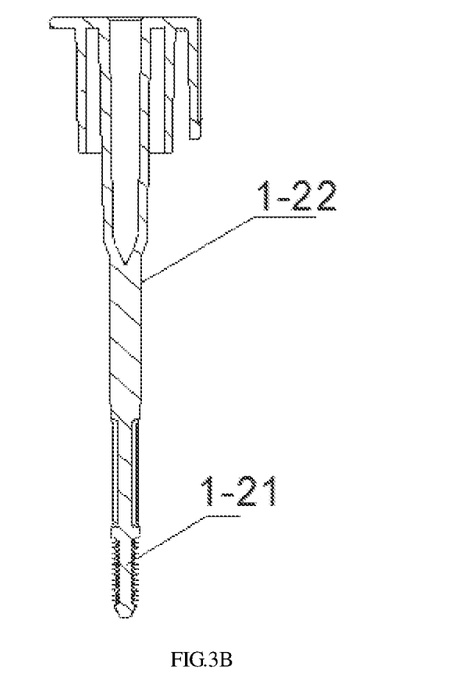
FIG. 3B is a perspective view of a sample feeding rod according to one embodiment of the present invention.

In some preferred embodiments, the sealing part 4-3 further comprises a barrier film 4-11 disposed at the outlet of the valve chamber 4-1, to enhance the reliability of the sealing part 4-3, as shown in FIG. 3B. The plug is inside and the barrier film 4-11 is outside, to achieve dual sealing and separation of the sampling chamber 1-1 and the detecting device. The "inside, outside" herein is relative to the valve chamber 4-1. When the push rod 4-2 is operating, the plug will pierce the barrier film 4-11 completely, to avoid the inaccurate quantification of samples caused by complete or partial sealing of sample feeding channel by the barrier film 4-11.

Sampling Device

The sampling device of the present invention can achieve quantitative sampling of solid and semi-solid samples, and it can mix the solid or semi-solid samples with a buffer solution, to form a sample mixture.

Figure 1B:
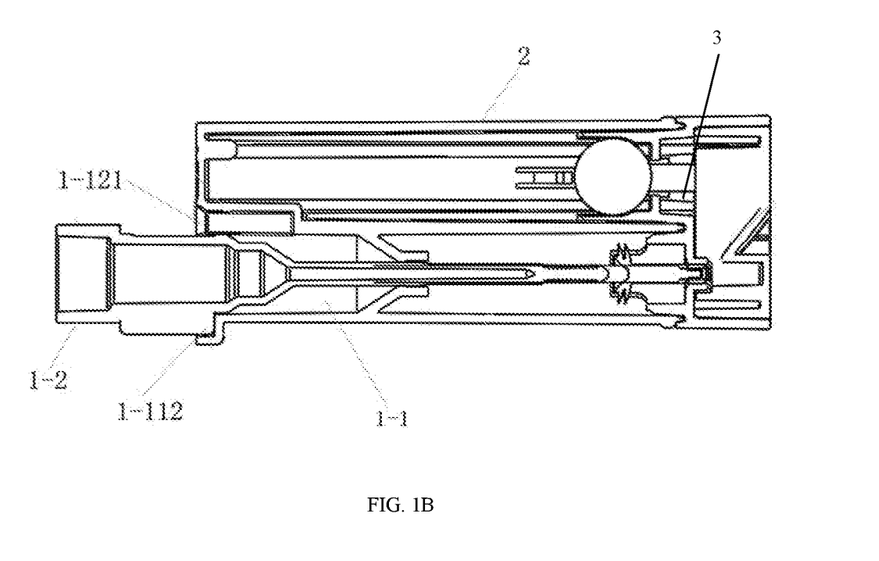
FIG. 1B is a cross-sectional view of FIG. 1A.
Figure 2B:
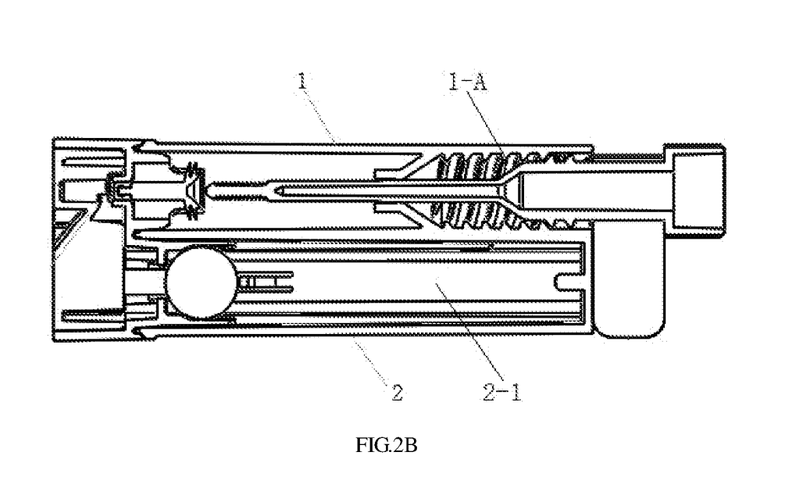
FIG. 2B is a cross-sectional view of FIG. 2A.

As shown in FIG. 1B, FIG. 2B and FIG. 3A, the sampling device comprises a sampling chamber 1-1 and a sample feeding rod 1-2. The sampling chamber 1-1 is used for accommodating the buffer solution for dissolving solid or semi-solid samples. The sample feeding rod 1-2 is used for acquiring solid or semi-solid samples. After obtaining samples, the sample feeding rod 1-2 is inserted into the buffer solution, and the samples are dissolved in the buffer solution, to form a sample mixture.

In some embodiments, as shown in FIG. 1B, FIG. 2B and FIG. 3A, the sampling chamber 1-1 is provided with a baffle 1-3, and the area between the baffle 1-3 and the valve assembly forms a sample mixing sub-chamber, and the baffle 1-3 is provided with a sample-passing hole 1-5 to allow the insertion of a sample feeding rod 1-2; the sample feeding rod 1-2 and sample-passing hole form a quantitative sampling unit. The buffer solution is injected to the sample mixing sub-chamber, and excessive samples in the sample feeding rod 1-2 are blocked by the wall of the sample-passing hole, so that they cannot enter the sample mixing sub-chamber, to achieve quantitative sampling.

Figure 1C:
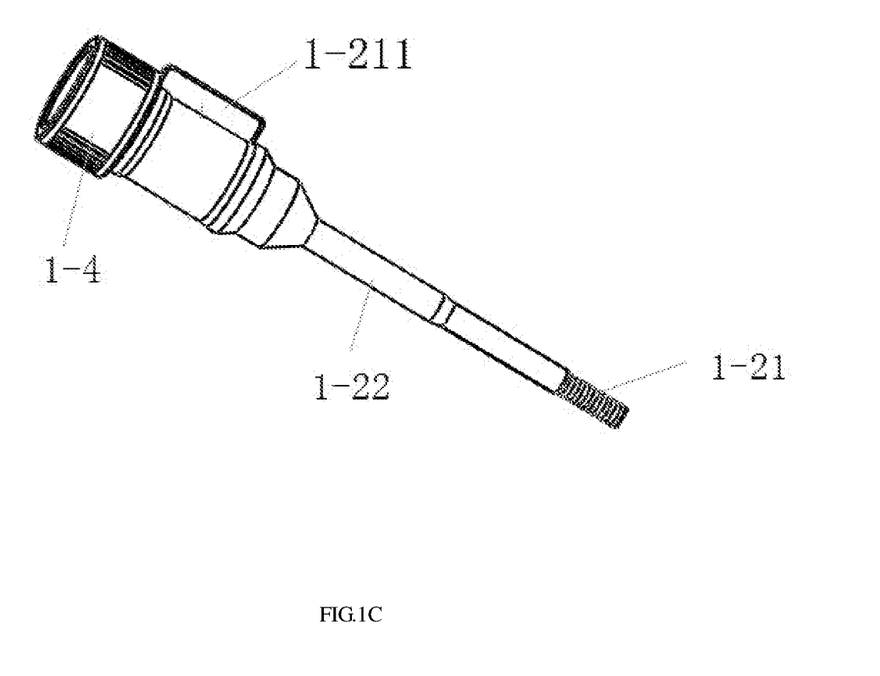
FIG. 1C is a perspective view of a sample feeding rod according to one embodiment of the present invention.
Figure 2C:
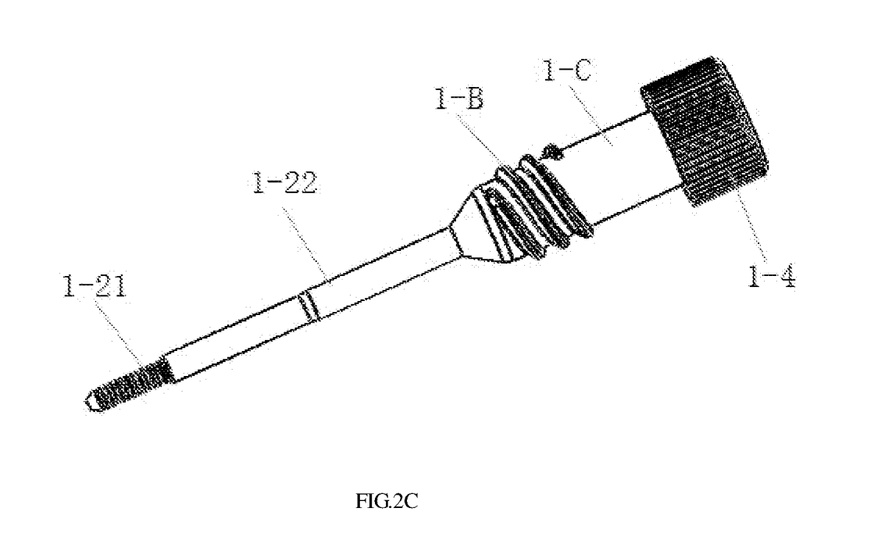
FIG. 2C is a perspective view of a sample feeding rod according to a second embodiment of the present invention.

In some preferred embodiments, as shown in FIGS. 1C, 2C and FIG. 6, the sample feeding rod 1-2 comprises a loading portion 1-21 and an inserting portion 1-22, and the loading portion 1-21 and the sample-passing hole 1-5 form a quantitative sampling unit. The inserting portion 1-22 has an increased diameter in a direction away from the loading portion 1-21, and the inserting portion 1-22 seals the sample-passing hole 1-5. The teeth and grooves of the loading portion 1-21 are distributed intermittently. The loading portion 1-21 is located at the bottom of the sample feeding rod 1-2, after samples on the sample loading portion 1-21 are dissolved, the loading portion 1-21 is in contact with the push rod 4-2 of the valve assembly, the loading portion 1-21 moves downward by abutting against the push rod 4-2, and the push rod 4-2 opens the sealing part 4-3 to start sample delivery. The sample feeding rod 1-2 continues to run, to deliver samples continuously. When the inserting portion 1-22 reaches the position of the sealed sample-passing hole 1-5, the baffle 1-3 abuts against the sample feeding rod 1-2, and the sample feeding rod 1-2 cannot continue running, in addition, the sample feeding rod 1-2 seals the sample mixing sub-chamber, so that the sample mixture will not be leaked. At the same time, the sealing portion 4-23 of the push rod 4-2 seals the valve chamber 4-1, to stop sample delivery.

In some preferred embodiments, a guide sleeve 1-31 is disposed below the baffle 1-3, the guide sleeve 1-31 is located at the sample-passing hole 1-5, and the guide sleeve 1-31 is integrated with the baffle 1-3. The guide sleeve 1-31 guides the sample feeding rod 1-2 to run in the axial direction.

Figure 7:
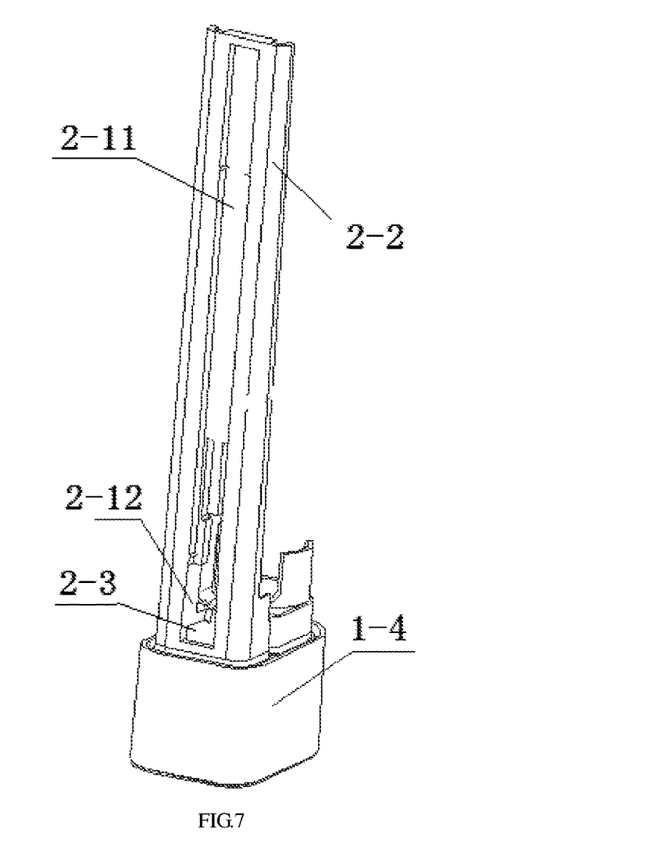
FIG. 7 is a perspective view of a combination of a testing element mounting rack and a valve chamber according to one embodiment of the invention.

In some preferred embodiments, as shown in FIG. 1C, FIG. 2C and FIG. 7, the sample feeding rod 1-2 is provided with a sample feeding cover 1-4, and the sample feeding cover 1-4 matches with the inlet of the sampling chamber 1-1. The sample feeding cover 1-4 can seal the opening of sampling chamber 1-1. The sampling chamber 1-1 is sealed by both the sample feeding cover 1-4 and sample feeding rod 1-2, to avoid the leakage of sample mixture.

Detecting Device

The detecting device can accommodate the sample mixture and testing element, so that the sample mixture is adsorbed by the testing element. The testing element can be used to detect samples, for example, detecting the presence or absence of analytes in the fecal samples.

As a preferred solution, as shown in FIG. 1B, FIG. 2B and FIG. 3A, the detecting device has a detection chamber 2-1, the detection chamber 2-1 is adjacent to the sampling chamber 1-1, and the detection chamber 2-1 is provided with a testing element mounting rack 2-2. The "adjacent" includes "horizontally adjacent" and "vertically adjacent", when the detection chamber 2-1 is adjacent horizontally to the sampling chamber 1-1, the communicating mechanism is located under detection chamber 2-1 and sampling chamber 1-1. When detection chamber 2-1 is vertically adjacent to sampling chamber 1-1, the communicating mechanism is located between detection chamber 2-1 and sampling chamber 1-1.

The detection chamber 2-1 has a vent 2-3, making the air pressure inside the detection chamber 2-1 in balance with the outside.

As a preferred solution, as shown in FIG. 6, the testing element mounting rack 2-2 is integrated with the valve chamber 4-1 and the stripping position 2-12 is on the testing element mounting rack 2-2.

As a preferred solution, as shown in FIG. 7, the testing element mounting rack 2-2 is provided with a mounting slot 2-11, and the mounting slot 2-11 communicates with a sample feeding channel. The testing element is placed in the mounting slot 2-11, the sampling area of the testing element is in the sample sub-chamber, and the detection result area of the testing element is in the detection sub-chamber.

As a preferred solution, as shown in FIG. 6, the detection chamber 2-1 is divided into a detection sub-chamber A and an accessory sub-chamber B by the testing element mounting rack 2-2. The stripping position 2-12 is a through hole, the accessory sub-chamber B is adjacent to the detection sub-chamber A, and the through hole communicates with the accessory sub-chamber B and the detection sub-chamber A. A desiccant and other accessories can be placed in the accessory sub-chamber B to adsorb the moisture in the detection chamber 2-1, to keep the testing element dry.

Anti-Misoperation Component

In order to prevent triggering delivery of samples by the valve assembly due to mistaken operation, an anti-misoperation component is provided between the sample delivery device and the detecting device.

Figure 8A:
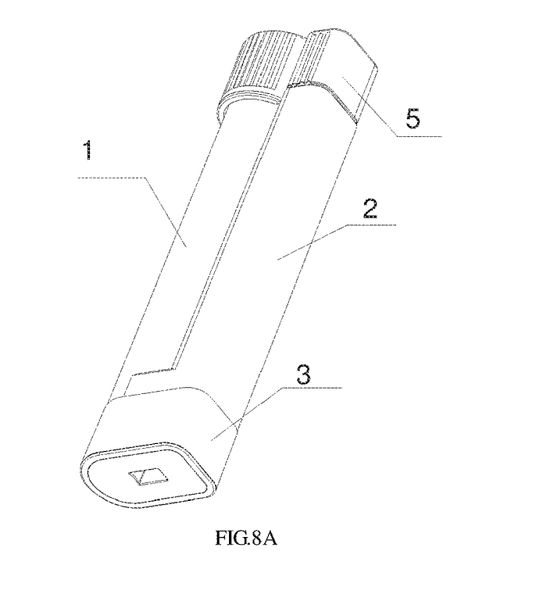
FIG. 8A is a perspective view according to a fourth embodiment of the present invention.
Figure 8B:
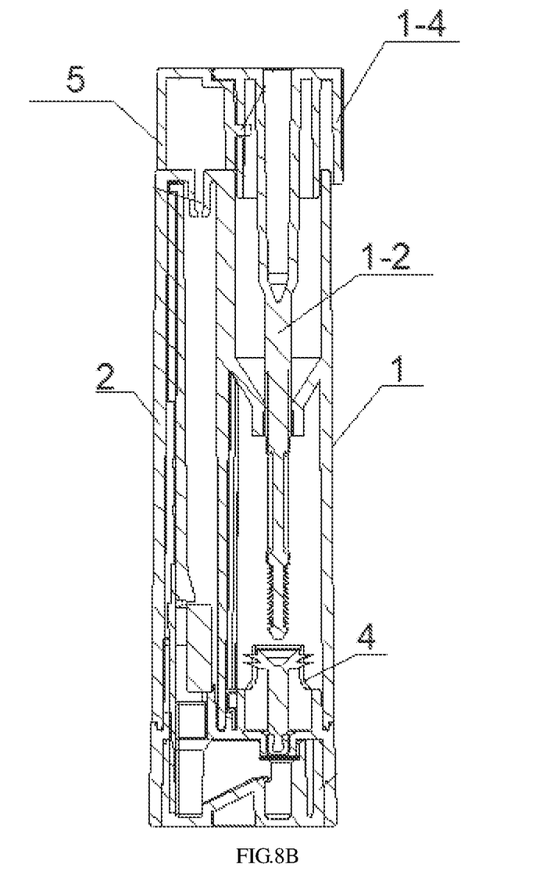
FIG. 8B is a cross-sectional view of FIG. 8A.

As a preferred embodiment, as shown in FIG. 8A and FIG. 8B, the sampling chamber 1-1 is located on the side of the detection chamber 2-1, the sample feeding rod 1-2 is detachably connected to a limiting cover 5, and when the limiting cover 5 is combined with the sample feeding rod 1-2, the limiting cover 5 is abutted against the detection chamber 2-1. Therefore, when the limiting cover 5 is used as an anti-misoperation component and the limiting cover 5 is combined with the sample feeding cover 1-4, the sample feeding rod 1-2 is unable to trigger the valve assembly; only when the limiting cover 5 is removed from the sample feeding rod 1-2, the sample feeding rod 1-2 can operate and trigger the valve assembly, to achieve anti-misoperation.

Sample feeding rod 1-2 is provided with a sample feeding cover 1-4 that matches with the inlet of sampling chamber 1-1. A notch that matches with the limiting cover 5 is provided on the sample feeding cover 1-4, and the notch forms an elastic bayonet; the limiting cover 5 is provided with a buckle, and the elastic bayonet is clamped with the buckle. By this way, the limiting block is combined with the sample feeding rod 1-2.

Pins and holes are established between the sample feeding rod 1-2 and the limiting cover 5. The pins are located in the sample feeding rod 1-2, and the holes are located in the limiting cover; or the pins are located in the limiting cover 5 and the holes are located in the sample feeding rod 1-2, to achieve the positioning of the sample feeding rod 1-2 and the limiting cover 5.

As a preferred embodiment, as shown in FIG. 1B and FIG. 1C, the sample feeding rod 1-2 has a convex block 1-211 thereon, the sampling chamber 1-1 has a limiting portion 1-112 for abutting the convex block 1-211 and an operating portion 1-121 for guiding the convex block 1-211. When the convex block 1-211 matches with the limiting portion 1-112, the sample feeding rod 1-2 is away from the valve assembly and unable to trigger the valve assembly; only when the convex block 1-211 matches with the operating portion 1-121, the convex block 1-211 runs along the operating portion 1-121, and the sample feeding rod 1-2 triggers the opening of the valve assembly. By this way, the convex block 1-211, limiting portion 1-112 and operating portion 1-121 can achieve anti-misoperation.

As a preferred embodiment, the limiting portion 1-112 is provided with a groove for accommodating the convex block 1-211 and abutting a stop portion of the convex block 1-211; the groove is located on the sampling chamber 1-1.

As a preferred embodiment, the operating portion 1-121 is a notch on the wall of the sampling chamber 1-1, and the notch allows the convex block 1-211 to operate therein.

As a preferred embodiment, the sampling chamber 1-1 is located on the side of the detection chamber 2-1, and the operating portion 1-121 is located between the sampling chamber 1-1 and the detection chamber 2-1.

As a preferred embodiment, as shown in FIGS. 2B and 2C, a thread pair is arranged between the sample feeding rod 1-2 and the sampling chamber 1-1, and the thread pair is located on the baffle 1-3. The thread 1-B on sample feeding rod 1-2 and thread 1-A on the sampling chamber together form a thread pair. In the initial state, the sample feeding rod 1-2 is limited by the thread pair at the position away from the valve assembly. Only when the sample feeding cover 1-4 is rotated by an external force can the sample feeding rod 1-2 moves down along the thread pair to open the valve assembly.

The length of thread 1-B on sample feeding rod 1-2 is less than the length of thread 1-A on sampling chamber 1-1. When the thread of sample feeding rod 1-2 is at the starting point of the thread of sampling chamber 1-1, the sample feeding cover 1-4 is away from the valve assembly. The process that the thread of sample feeding rod 1-2 starts from the staring point of the thread of sampling chamber 1-1 to the end point is the process that the sample feeding rod 1-2 pushes the push rod 4-2 to open valve chamber 4-1 to deliver samples, and close the n valve chamber 4-1 after sample delivery.

As a preferred embodiment, as shown in FIG. 2A, FIGS. 2B and 2C, the detection chamber 2-1 is located on the side of the sampling chamber 1-1, the sample feeding rod 1-2 has a thread segment 1-B and a polish segment 1-C, the polish segment 1-C is on the thread segment 1-B, and the polish segment 1-C is detachably provided with an anti-misoperation block 1-6, as shown in FIG. 2A-3B, on one end of the anti-misoperation block 1-6 is a flexible buckle 1-6A and another end is a rigid block 1-6B. When the anti-misoperation block 1-6 is combined with a sample feeding rod 1-2, the detection chamber 2-1 abuts against the rigid block 1-6B. The flexible buckle 1-6A is clamped with the polish segment 1-C, while the rigid block 1-6B is abutted by the detecting device to limit the displacement.

In order to further ensure that the valve assembly is not triggered by the misoperation, the flexible buckle of the anti-misoperation block is stuck in the polish segment 1-C of the anti-misoperation portion 1-121, and the rigid block 1-6B is restricted to move downward by the detecting device. When the flexible buckle 1-6A is combined with the polish segment 1-C, the sample feeding cover cannot drive the sample feeding rod 1-2 to move downward. Only when the flexible buckle is removed from the polish segment will the sample feeding rod 1-2 be able to move down while rotating.

Detection Method

The method for detecting analytes in the solid or semi-solid samples is described below in combination with the accompanying drawings.

A collection and detection device is prepared, for example, the collection and detection device, as shown in FIG. 1C, FIG. 2B or FIG. 3A, comprises a container integrating a sampling chamber 1-1, a detection chamber 2-1 and a communicating mechanism, and a testing element arranged inside the detection chamber 2-1, and a buffer solution injected into the sampling chamber 1-1 and a sample feeding rod 1-2; an anti-misoperation component is mounted on the sample feeding rod 1-2, and the sample feeding rod 1-2 is in an inoperable position.

The sample feeding rod 1-2 is taken out so that samples are attached on the loading portion 1-21; insert the sample feeding rod 1-2 into the sampling chamber 1-1, and when the loading portion 1-21 passes sample-passing hole, surplus samples will be blocked by the baffle and unable to mix with the buffer solution, to complete the quantitative sampling. When transporting the samples, the sample feeding rod 1-2 is equipped with an anti-misoperation component, and the sample feeding rod 1-2 seals the sampling chamber.

When testing, the anti-misoperation component is removed or placed to a place allowing running of sample feeding rod 1-2, to push the sample feeding rod 1-2, and open the valve assembly. The sample mixture flows to the loading area of the testing element to complete the sample testing. After samples are delivered, the sample feeding rod 1-2 is pushed to the position abutting against the sampling chamber 1-1, to stop sample delivery and complete the quantitative delivery of samples.

The invention shown and described herein may be implemented in the absence of any elements, limitations specifically disclosed herein. The terms and expressions used herein are for illustration rather than limitation, which do not exclude any equivalents of the features and portions described herein in the use of these terms and expressions, in addition, it should be understood that various modifications are feasible within the scope of the present invention. It is therefore to be understood that, although the invention has been particularly disclosed by various embodiments and alternative features, modifications and variations of the concepts described herein may be employed by those of skilled in the art, and such modifications and variations will fall into the scope of protection of the present invention as defined by the appended claims.

The contents of the articles, patents, patent applications, and all other documents and electronic information available or documented herein are incorporated herein by reference in their entirety, as if each individual publication is specifically and individually indicated for reference. The applicant reserves the right to incorporate any and all materials and information from any such article, patent, patent application or other document into this application.

What is claimed is:

1. A sample collection detector, comprising:
    a sampling device, a detecting device and a communicating device,
    wherein the sampling device has a sampling chamber and a sample feeding rod, the sample feeding rod is inserted into the sampling chamber to finish sampling;
    the communicating device has a sample feeding channel that is in communication with the sampling chamber and detecting device,
    a valve assembly is provided between the sample feeding channel and the sampling chamber, the valve assembly is initially closed, the sample feeding channel is separated from the sampling chamber, the sample feeding rod triggers the valve assembly to open and communicate the sample feeding channel and the sampling chamber, wherein the valve assembly comprises a valve chamber, a push rod and a sealing part, the valve chamber is connected with the sampling chamber and the sample feeding channel, and the sealing part seals an outlet of the valve chamber; the communicating device has provided a space for running the push rod.

2. The sample collection detector according to claim 1, wherein the sampling chamber is provided with a baffle, and the area between the baffle and the valve assembly forms a sample mixing sub-chamber, and the baffle is provided with a sample-passing hole to allow insertion of the sample feeding rod; the sample feeding rod comprises a loading portion and an inserting portion, and the loading portion and the sample-passing hole form a quantitative sampling unit.

3. The sample collection detector according to claim 1, wherein the detecting device has a detection chamber, the detection chamber is adjacent to the sampling chamber, and the detection chamber is provided with a testing element mounting rack; the testing element mounting rack is integrated with the valve chamber and a stripping position is on the testing element mounting rack.

4. The sample collection detector according to claim 1, wherein the sampling chamber is located on a side of the detection chamber, the sample feeding rod is detachably connected to a limiting cover, and when the limiting cover is combined with the sample feeding rod, the limiting cover is abutted against the detection chamber.

5. The sample collection detector according to claim 1, wherein the sample feeding rod has a convex block thereon, the sampling chamber has a limiting portion for abutting the convex block and an operating portion for guiding the convex block; the limiting portion is provided with a groove for accommodating the convex block and abutting a stop portion of the convex block; the groove is located on the sampling chamber.

6. The sample collection detector according to claim 1, wherein the push rod comprises a receiving portion and a sample-passing portion, and when the valve assembly is opened, the receiving portion is operated with the pressure of the sample feeding rod; the sample-passing portion conveys the pressure to a sealing part, and a sample-passing groove is provided on an outer surface of the sample-passing portion.

7. The sample collection detector according to claim 6, wherein the push rod has a sealing portion located between the receiving portion and the sample-passing portion, and the sealing portion has a size of interference fit with the outlet of the valve chamber; the receiving portion is a piston, the piston has a disc-shaped fin extending outward, and the disc-shaped fin is a flexible part.

8. The sample collection detector according to claim 1, wherein the push rod comprises a receiving portion and a sample-passing portion, and when the valve assembly is opened, the receiving portion is operated with the pressure of the sample feeding rod; the sample-passing portion conveys the pressure to a sealing part, and a sample-passing groove is provided on an outer surface of the sample-passing portion.

9. The sample collection detector according to claim 8, wherein the push rod has a sealing portion located between the receiving portion and the sample-passing portion, and the sealing portion has a size of interference fit with the outlet of the valve chamber; the receiving portion is a piston, the piston has a disc-shaped fin extending outward, and the disc-shaped fin is a flexible part.

10. The sample collection detector according to claim 1, wherein the sealing part comprises a plug that independently plugs the valve chamber; or the sealing part comprises a plug mounted on the push rod.

11. The sample collection detector according to claim 10, wherein the sealing part further comprises a barrier film disposed at the outlet of the valve chamber.

12. The sample collection detector according to claim 1, wherein a thread pair is arranged between the sample feeding rod and the sampling chamber, and the thread pair is located on a baffle.

13. The sample collection detector according to claim 12, wherein the detection chamber is located on the side of the sampling chamber, the sample feeding rod has a thread segment and a polish segment, the polish segment is on the thread segment, and the polish segment is detachably provided with an anti-misoperation block, when the anti-misoperation block is combined with a sample feeding rod, one end of the anti-misoperation block is connected, and the other end abuts against the detection chamber.

14. The sample collection detector according to claim 13, wherein the anti-misoperation block has a flexible buckle at one end and a rigid block at the other end.

* * * * *